United States Patent [19]

Cheung et al.

[11] Patent Number: 5,659,107
[45] Date of Patent: Aug. 19, 1997

[54] SEPARATION OF CYCLOPENTADIENE FROM DICYCLOPENTADIENE

[75] Inventors: Tin-Tack Peter Cheung; Marvin M. Johnson, both of Bartlesville, Okla.

[73] Assignee: Phillips Petroleum Company, Bartlesville, Okla.

[21] Appl. No.: 646,433

[22] Filed: May 7, 1996

[51] Int. Cl.⁶ ............................ C07C 7/00; C07C 7/12
[52] U.S. Cl. ..................... 585/824; 585/820; 585/823
[58] Field of Search ................................. 585/824, 820

[56] References Cited

U.S. PATENT DOCUMENTS

| | | | |
|---|---|---|---|
| 3,674,883 | 7/1972 | Schleppinghoff et al. | 585/362 |
| 3,719,718 | 3/1973 | Grude et al. | 585/354 |
| 4,390,742 | 6/1983 | Wideman | 585/854 |
| 4,392,004 | 7/1983 | D'Sidocky | 585/820 |
| 4,438,289 | 3/1984 | D'Sidocky | 585/820 |
| 4,471,153 | 9/1984 | Throckmorton | 585/850 |
| 4,584,425 | 4/1986 | Tom | 585/827 |
| 4,751,337 | 6/1988 | Espy et al. | 585/362 |
| 5,245,108 | 9/1993 | Van Deursen et al. | 585/820 |
| 5,378,783 | 1/1995 | Okumura et al. | 585/851 |
| 5,401,891 | 3/1995 | Keenan et al. | 585/318 |

OTHER PUBLICATIONS

"Selexsorb® COS Selective Adsorbent" product brochure of Alcoa Separations Technology Division, May 1988.

*Primary Examiner*—Ellen M. McAvoy
*Attorney, Agent, or Firm*—Karl K. Brandes; Lucas K. Shay

[57] ABSTRACT

Cyclopentadiene is separated from dicyclopentadiene by means of a sorbent material which contains (i) alkali metal oxide(s) and/or hydroxide(s) and (ii) an inorganic support material. The more preferred sorbent material is $Na_2O$ and/or NaOH on alumina.

20 Claims, No Drawings

SEPARATION OF CYCLOPENTADIENE FROM DICYCLOPENTADIENE

BACKGROUND OF THE INVENTION

This invention relates to an adsorption/absorption process for removing cyclopentadiene from a hydrocarbon stream containing both cyclopentadiene and dicyclopentadiene.

Dicyclopentadiene is formed as a by-product in various chemical processes, e.g., in the pyrolysis of ethane and higher alkanes to monoolefins (ethylene, propylene). The higher boiling fraction of this pyrolysis product contains aromatics, higher paraffins (pyrolysis gasoline), and cyclic diolefins, such as cyclopentadiene (CPD; $C_5H_6$) and dicyclopentadiene (DCPD; $C_{10}H_{12}$). When DCPD is separated by fractional distillation from other hydrocarbons present in this pyrolysis production fraction, small amounts of CPD are generally present as impurities in the DCPD stream. For some end-uses of DCPD (e.g., for making polyesters), the presence of CPD is detrimental. Thus, there is an ever present need to separate CPD from DCPD so as to obtain DCPD in sufficiently high purity for certain end-uses. The present invention is directed to an effective process for separating CPD from DCPD.

SUMMARY OF THE INVENTION

It is an object of this invention to separate cyclopentadiene from dicyclopentadiene. It is a specific object to remove cyclopentadiene from a hydrocarbon fluid which comprises dicyclopentadiene as the major component. Other objects and advantages will be apparent from the detailed description and the appended claims.

In accordance with this invention, a process for separating cyclopentadiene from dicyclopentadiene comprises contacting (a) a fluid hydrocarbon-containing feed comprising both cyclopentadiene and dicyclopentadiene with (b) a solid sorbent composition comprising (i) at least one alkaline compound selected from the group consisting of alkali metal oxides and alkali metal hydroxides and (ii) an inorganic support material at effective separation conditions so as to obtain a fluid hydrocarbon-containing product in which cyclopentadiene is present at a lower concentration than in said fluid feed.

DETAILED DESCRIPTION OF THE INVENTION

The sorbent composition employed in the separation process of this invention comprises (i) at least one alkali metal oxide and/or hydroxide (preferably sodium oxide, sodium hydroxide, potassium oxide, potassium hydroxide or mixtures of two or more than two of these Group IA metal compounds) and (b) at least one inorganic support material, preferably selected from the group consisting of alumina, silica, silica-alumina, aluminum phosphate, clays, zeolites, titania, hafnia, zirconia, oxides of Group IIA metals (such as MgO, CaO, SrO, BaO), carbonates of Group IIA metals (such as $MgCO_3$, $CaCO_3$, $SrCO_3$, $BaCO_3$), carbonates of Group IA metals (such as $Li_2CO_3$ and the like), oxides of Group IIIB metals (such as $Sc_2O_3$, $La_2O_3$, $CeO_2$), magnesium aluminate, calcium aluminate, zinc oxide, zinc aluminate, zinc titanate, iron oxide, activated carbon, and mixtures of two or more than two of these compounds. The more preferred inorganic support material is alumina, which most preferably is amorphous alumina or chi alumina or gamma alumina.

Preferably, the sorbent composition has a surface area (determined by the BET method using $N_2$) of about 200–500 (more preferably about 300–400) $m^2$/gram, a total pore volume of about 0.2–1.0 (more preferably about 0.3–0.8) cc/gram, and a packed bulk density of about 30–60 lb/ft$^3$. The particle size of the sorbent material (preferably spheres) generally is in the range of about 2 to about 10 (preferably about 3–5) mm. The content of "loss on ignition" (determined at 250°–1200° C.) in the sorbent material generally is about 2–8 weight-%. The content of alkali metal oxide and/or hydroxide (more preferably $Na_2O$ or NaOH or mixtures thereof) in the sorbent composition generally is about 0.1–5 (preferably about 0.4–2.0) weight-%. More preferably, the alumina content in the sorbent material is about 93–96 weight-%, with only traces (i.e., less than about 0.1 weight-%) of other inorganic support material being present. A preferred commercial sorbent material, which comprises $Na_2O$ and $Al_2O_3$, is available from Alcoa Adsorbents and Catalyst Materials, Warrendale, Pa., under the product designation "Selexsorb® COS Selective Adsorbent".

Generally, the feed is liquid and contains at least 50 weight-%, preferably more than 80 weight-%, and more preferably about 90–98 weight-% dicyclopentadiene (DCPD), wherein the amount of the endo-DCPD generally far exceeds the amount of exo-DCPD. Preferably, the ratio of endo-DCPD to exo-DCPD in the feed is about 80:1 to about 99:1. The term "dicyclopentadiene", as used herein, encompasses the endo and exo forms of DCPD. The amount of cyclopentadiene (CPD) in the feed generally is less than about 1 weight-%, and preferably is in the range of about 0.002 to about 0.1 (more preferably about 0.005–0.02) weight-%. Small amounts of aromatics (such as 0.1–0.2 weight-% propylbenzene) and about 1–10 weight-% of other non-aromatic cyclic compounds (generally $C_{10-11}$ bi- and tricyclic monoolefins and diolefins) can also be present in the feed.

The separation process of this invention can be carried out in any suitable manner which affords the removal of all or a major portion of CPD present in the feed. Generally, the feed (preferably liquid) is contacted with the sorbent composition at a temperature in the range of about 10° C. to about 100° C., generally at atmospheric pressure conditions (0 psig). Preferably, the sorbent material has been calcined (generally at a temperature of about 200°–300° C. for about 0.5 to about 20 hours, preferably about 1–10 hours)prior to its use. The sorption process of this invention can be carded out as a batch process, wherein solid sorbent and liquid feed are mixed and, preferably, agitated, followed by conventional separation of the liquid phase (which contains less CPD than the feed) and the solid phase (which contained ad-/absorbed CPD). Generally, the weight ratio of the fluid (preferably liquid) feed to the solid sorbent material is about 1:1 to about 50:1. In a commercial operation, it is generally preferred to operate in a continuous mode by passing the liquid feed through a column containing the solid sorbent material, wherein the exiting effluent contains less CPD than the feed. Any suitable weight hourly space velocity (lb feed per lb sorbent per hour) can be employed. Preferably, this weight hourly space velocity is about 0.5–5 lb/lb/hour. When the CPD-sorption capacity of the sorbent material has been reached, the spent sorbent can be discarded or regenerated (e.g., by heating it to about 400°–700° C. for about 1–24 hours).

The following example is presented to further illustrate this invention and is not to be construed as unduly limiting its scope.

EXAMPLE

A sample of 10 cc of a liquid feed which contains about 92 weight-% DCPD and about 0.01 weight-% (about 100 ppm) CPD is mixed with 2 grams of spherical, 1/16 inch Selexsorb® COS Selective Adsorbent (obtained from Alcoa Adsorbents and Catalyst Materials, Separations Technology Division, 181 Thorn Hill Road, Warrendale, Pa.) which had been heated for 2 hours at 200°–300° C. The feed/sorbent mixture was shaken, and samples of the liquid were taken after 24 hours and 72 hours, respectively. These samples were analyzed by means of a gas chromatograph. Test results are summarized in Table I.

TABLE I

| | Composition (Wt %) | | |
| --- | --- | --- | --- |
| | | Product Obtained After | |
| Compound | Feed | 24 Hours | 72 Hours |
| Cyclopentadiene | 0.014 | <0.002 | <0.002 |
| endo-Dicyclopentadiene | 90.9 | 91.9 | 91.2 |
| exo-Dicyclopentadiene | 1.0 | 1.0 | 1.0 |
| Cyclic $C_{10}$–$C_{11}$ Hydrocarbons | 7.9 | 7.7 | 7.7 |
| Propylbenzene | 0.1 | 0.1 | 0.1 |

Test results in Table I clearly show that an essentially complete removal of CPD was achieved, whereas no significant change in the concentration of the other liquid components (in particular, endo-DCPD) was detected.

Reasonable variations, modifications and adaptations for various usages and conditions can be made within the scope of the disclosure and the appended claims, without departing from the scope of this invention.

That which is claimed:

1. A process for separating cyclopentadiene from dicyclopentadiene which comprises contacting (a) a fluid hydrocarbon-containing feed comprising said cyclopentadiene and said dicyclopentadiene with (b) a solid sorbent composition comprising (i) at least one alkaline compound selected from the group consisting of alkali metal oxides and alkali metal hydroxides and (ii) an inorganic support material at effective separation conditions, so as to obtain a liquid hydrocarbon-containing product in which the concentration of said cyclopentadiene is lower than in said feed wherein said inorganic support material is selected from the group consisting of alumina, silica, silica-alumina, aluminum phosphate, clays, zeolites, titania, hafnia, zirconia, oxides of Group IIA metals, carbonates of Group IIA metals, carbonates of Group IA metals, oxides of Group IIIB metals, magnesium aluminate, calcium aluminate, zinc oxide, zinc aluminate, zinc titanate, iron oxide, and mixtures of two or more thereof.

2. A process in accordance with claim 1, wherein said at least one alkaline compound is selected from the group consisting of sodium oxide, sodium hydroxide, potassium oxide, potassium hydroxide, and mixtures of two or more than two of these Group IA metal compounds.

3. A process in accordance with claim 2, wherein the content of said at least one alkaline compound in said sorbent composition is about 0.1–5 weight-%.

4. A process in accordance with claim 2, wherein said at least one alkaline compound is selected from the group consisting of sodium oxide and sodium hydroxide and mixtures thereof, and said inorganic support material is alumina.

5. A process in accordance with claim 4, wherein the content of said at least one alkaline metal is about 0.4–2.0 weight-%.

6. A process in accordance with claim 1, wherein said fluid hydrocarbon-containing feed is liquid.

7. A process in accordance with claim 6, wherein said liquid feed contains at least about 50 weight-% dicyclopentadiene and less than about 1 weight-% cyclopentadiene.

8. A process in accordance with claim 7, wherein said liquid feed contains more than about 80 weight-% dicyclopentadiene and about 0.002–0.1 weight-% cyclopentadiene.

9. A process in accordance with claim 8, wherein said liquid feed contains about 90–98 weight-% dicyclopentadiene and about 0.005–0.02 weight-% cyclopentadiene.

10. A process in accordance with claim 1, wherein said effective separation conditions comprise a temperature of about 10° C. to about 100° C.

11. A process in accordance with claim 10, wherein said process is a batch process and said fluid hydrocarbon-containing feed is liquid.

12. A process in accordance with claim 11, wherein the weight ratio of said liquid feed to said solid sorbent composition is about 1:1 to about 50:1.

13. A process in accordance with claim 10, wherein said process is a continuous process and said fluid hydrocarbon-containing feed is liquid.

14. A process in accordance with claim 13, wherein the weight hourly space velocity of said liquid feed is about 0.5–5 lb feed per lb sorbent composition per hour.

15. A process in accordance with claim 1, wherein said solid sorbent composition has been calcined at a temperature of about 200°–300° C. for a time period of about 0.5–20 hours prior to its use in said process.

16. A process for separating cyclopentadiene from dicyclopentadiene comprising contacting (a) a fluid hydrocarbon-containing feed comprising said cyclopentadiene and said dicyclopentadiene with (b) a solid sorbent composition comprising (i) at least one alkaline compound selected from the group consisting of alkali metal oxides and alkali metal hydroxides and (ii) an inorganic support material under conditions effective to obtain a liquid hydrocarbon-containing product in which the concentration of said cyclopentadiene is lower than in said feed wherein said inorganic support material is selected from the group consisting of alumina, silica, silica-alumina, aluminum phosphate, clays, zeolites, titania, hafnia, zirconia, oxides of Group IIA metals, carbonates of Group IIA metals, carbonates of Group IA metals, oxides of Group IIIB metals, magnesium aluminate, calcium aluminate, zinc oxide, zinc aluminate, zinc titanate, iron oxide, and mixtures of two or more thereof;

said at least one alkaline compound is selected from the group consisting of sodium oxide, sodium hydroxide, potassium oxide, potassium hydroxide, and mixtures of two or more thereof; and the content of said at least one alkaline compound in said solid sorbent is about 0.1 to about 5 weight %.

17. A process in accordance with claim 16 wherein said fluid hydrogen-containing feed is liquid and comprises at least about 80 weight % dicyclopentadiene and less than about 1 weight % cyclopentadiene; said at least one alkaline compound is selected from the group consisting of sodium oxide, sodium hydroxide, and mixtures thereof; and the content of said at least one alkaline compound is about 0.4 to about 2 weight %.

18. A process in accordance with claim 17 wherein said fluid hydrogen-containing feed contains about 90 to about 98 weight % dicyclopentadiene and about 0.005 to about 0.02 weight % cyclopentadiene; said process is carried out at a temperature in the range of from about 10° C. to about 100° C.; and said solid sorbent comprises sodium oxide and alumina.

19. A process in accordance with claim 16 wherein said solid sorbent composition has been calcined at a temperature of about 200°–300° C. for a time period of about 0.5–20 hours prior to its use in said process.

20. A process for removing cyclopentadiene from a dicyclopentadiene-containing liquid feed comprising contacting said feed with a sorbent at about 10° C. to about 100° C. wherein said feed comprises more than about 90 weight % of dicyclopentadiene; said sorbent comprises alumina and about 0.4 to about 2 weight % of sodium oxide; and said sorbent has been calcined at about 200° C. to about 300° C. for about 1 to about 10 hours before being contacted with said feed.

* * * * *